(12) United States Patent
Park et al.

(10) Patent No.: US 8,026,343 B2
(45) Date of Patent: Sep. 27, 2011

(54) ANTIBODY MODULATING THE DIFFERENTIATION AND FUNCTION OF DENDRITIC CELLS VIA BINDING INTERCELLULAR ADHESION MOLECULE-1 AND USE THEREOF

(75) Inventors: Seong-Hoe Park, Seoul (KR); Kyeong-Cheon Jung, Seoul (KR); Youngmee Bae, Seoul (KR); Seong-Pyo Park, Seoul (KR); Yoon-Kyung Jeon, Gyeinggi-do (KR)

(73) Assignee: Dinona Inc., Seoul (KR)

( * ) Notice: Subject to any disclaimer, the term of this patent is extended or adjusted under 35 U.S.C. 154(b) by 372 days.

(21) Appl. No.: 12/410,426

(22) Filed: Mar. 24, 2009

(65) Prior Publication Data

US 2010/0168394 A1     Jul. 1, 2010

Related U.S. Application Data

(60) Provisional application No. 61/087,265, filed on Aug. 8, 2008.

(51) Int. Cl.
*C12P 21/08* (2006.01)
(52) U.S. Cl. .................. 530/387.3; 435/326; 530/388.1
(58) Field of Classification Search ............... 530/387.3, 530/388.1; 435/326
See application file for complete search history.

(56) References Cited

U.S. PATENT DOCUMENTS 5,695,760 A * 12/1997 Faanes et al. ............. 424/178.1

FOREIGN PATENT DOCUMENTS

| AU | 88228/91 B2 | 6/1992 |
| WO | WO 2005/086568 A2 | 9/2005 |

OTHER PUBLICATIONS

Lineberger et al. "Antibodies That Block Rhinovirus Attachment Map to Domain 1 of the Major Group Receptor", *J. Virol.* 64(6):2582-2587 (1990).
McClelland et al., Identification of monoclonal antibody epitopes and critical residues for rhinovirus binding in domain 1 of intercellular adhesion molecule 1, *PNAS* 88:7993-7997 (1991).
Application No. PCT/KR09/002019, International Search Report and Written Opinion of the International Searching Authority, mailed Sep. 16, 2009.

* cited by examiner

*Primary Examiner* — Misook Yu
*Assistant Examiner* — Brad Duffy
(74) *Attorney, Agent, or Firm* — Alston and Bird LLP

(57) ABSTRACT

The present invention relates to an antibody binding to human intercellular adhesion molecule-1 (ICAM-1) where the antibody is able to modulate the differentiation status of dendritic cells and prolong the graft survival. In addition, the present invention provides a pharmaceutical composition comprising the antibody, and method of using them for the treatment of disease.

11 Claims, 8 Drawing Sheets

ANTIBODY MODULATING THE DIFFERENTIATION AND FUNCTION OF DENDRITIC CELLS VIA BINDING INTERCELLULAR ADHESION MOLECULE-1 AND USE THEREOF

CROSS-REFERENCE TO RELATED APPLICATION

The present application claims priority to and the benefit of U.S. Ser. No. 61/087,265, filed Aug. 8, 2008 with United States Patent and Trademark Office which is hereby incorporated by reference for all purposes as if fully set forth herein.

REFERENCE TO A SEQUENCE LISTING

This application includes a Sequence Listing provided in ASCII text file named "SEQLIST.txt" which is of size 2340 bytes and created on Mar. 24, 2009, which is hereby incorporated by reference in its entirety for all purposes.

FIELD OF THE INVENTION

The present invention provides, among other things, antibodies binding to human intercellular adhesion molecule 1 (ICAM-1). Preferred antibodies are able to modulate the differentiation and function of dendritic cells and prolong the graft survival. Pharmaceutical composition comprising the antibodies, and methods of using them for the treatment of disease are also provided.

BACKGROUND OF INVENTION

ICAM-1 is a 90 kDa type I cell surface glycoprotein composed of five extracellular immunoglobulin superfamily domains referred to as domains 1 through 5 and numbered from N to C-terminus, a transmembrane region and an intracellular region (Cell. 1990, 61:243-54). ICAM-1 mediates leukocyte/leukocyte interaction such as interaction between T cells and antigen presenting cells. It also mediates leukocyte extravasation into tissue during inflammatory processes (Transplantation. 1999, 67:729-736). In vitro study showed that antibodies interfering the ICAM-1/leukocyte function antigen-1 (LFA-1) interaction are able to inhibit T cell adhesion to endothelial cells and T cell activation also could be significantly reduced in a mixed lymphocyte reaction by these antibodies (Proc. Natl. Acad. Sci. USA. 1988, 85:3095-3099). In monkey studies using murine monoclonal antibodies against human ICAM-1, R6-5-D6 (enlimomab), renal allograft survival has been prolonged and T cell infiltration in the graft was decreased compared with controls (J. Immunol. 1990, 144:4604-4612). Enlimomab also had been proved to be beneficial in depressing disease activity in patient with rheumatoid arthritis (Arthritis Rheum. 1994, 37:992-999; J. Rheumatol. 1996, 23:1338-1344). However, enlimomab induction therapy after renal transplantation in a randomized multicenter study was not able to reduce the rate of acute rejection or the risk of delayed onset of graft function (Transplantation 1999, 67:729-736). Moreover, clinical trial in acute ischemic stroke patient revealed that anti-ICAM-1 therapy with enlimomab was not an effective and indeed significantly worsen stroke outcome and induced more adverse effect, primarily infections and fever compared with placebo (Neurology 2001, 57:1428-1434). The enlimomab functions by blocking the adhesion of T cells as wells as neutrophils to the vascular endothelial cells and thus it has been suggested that interfering with neutrophil emigration potentially increases the susceptibility to infection (J. Immunol. 1999, 162:2352-2357).

Dendritic cells (DCs) are highly specialized antigen-presenting cells that integrate a variety of immune response (Nature 1998, 382:245-252), and include a heterogeneous family of professional antigen presenting cells involved in initiation of immunity and immunologic tolerance. Until now, immature DCs were believed to induce T-cell anergy, whereas DCs transformed into mature DCs by activation stimuli such as lipopolysaccharide (LPS) were thought to induce primary T cell response (Blood 2006, 108:1435-1440). Furthermore, semimature DCs with a distinctive cytokine production profile might be endowed with tolerogenic functions (Blood 2006, 108:1435-1440).

ICAM-1 is expressed in dendritic cells in high level. Until now, however, ICAM-1 in dendritic cells has been considered to serves as a simple adhesion molecule for LFA-1 binding during T cell-DC interaction.

SUMMARY OF THE INVENTION

One object of the present invention, among others, is to provide an antibody binding to human intercellular adhesion molecule 1 (ICAM-1) where the antibody is able to modulate the differentiation and function of dendritic cells and prolong the graft survival. In addition, the present invention provides a pharmaceutical composition comprising the antibody, and method of using them for the treatment of disease.

More particularly, the present invention provides an anti-human ICAM-1 antibody that suppresses rejection of transplanted cells or organs, or suppresses graft versus host disease by transplanted hematopoietic cells. The invention further provides such an antibody capable of binding domain 1 of human ICAM-1 but not blocking the interaction between ICAM-1 and its ligand, LFA-1.

The invention further provides a method for producing the material, and it provides cells producing the antibody or its fragment. The invention also includes the hybridoma cell, and the antibody produced by the hybridoma cell, obtained by the method.

The present invention also includes a pharmaceutical composition for suppressing rejection of transplanted cells or organs. The pharmaceutical composition is comprised of an immunosuppressive agent selected from the group consisting of: an antibody capable of binding ICAM-1 but not inhibiting the interaction of ICAM-1 and LFA-1; and a fragment of an antibody, the fragment being capable of binding ICAM-1 but not inhibiting the interaction of ICAM-1 and LFA.

Further, the present invention also provides a method for suppressing the rejection of transplanted cells or organs, or suppresses graft versus host disease by transplanted hematopoietic cells using an immunosuppressive agent, which is selected from the group consisting of antibody or antibody fragments. The antibody or the antibody fragment is preferably selected from the group consisting of monoclonal and polyclonal antibodies, and more preferably it is a human or animal (i.e., non-human) antibody.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawing, wherein.

DETAILED DESCRIPTION

Figure 1:
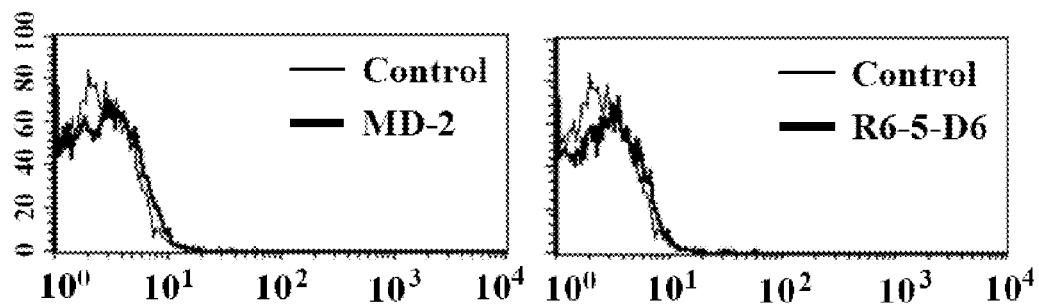
FIG. 1 shows a photograph of the reactivity of MD-2 and R6-5-D6 monoclonal antibodies on the surface of human ICAM-1-transfected HEK293T cells using single color flow cytometry.
Figure 1:
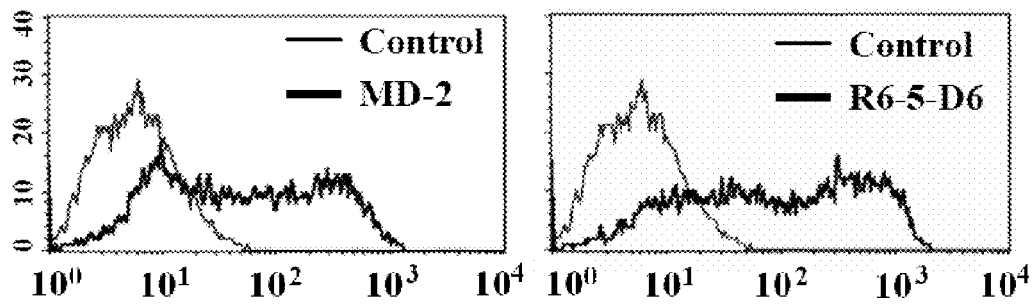

The present invention is further explained in more detail with reference to the following examples. These examples, however, should not be interpreted as limiting the scope of the present invention in any manner.

The present invention relates to a mouse anti-human ICAM-1 monoclonal antibody, MD-2 and fragments of MD-2 capable of inhibiting immune response. More particularly, the present invention relates to anti-human ICAM-1 antibody that suppresses rejection of transplanted cells or organs, or suppresses graft versus host disease by transplanted hematopoietic cells.

The invention further provides an antibody capable of binding domain 1 of human ICAM-1 but not blocking the interaction between ICAM-1 and its ligand, LFA-1. The invention also includes a hybridoma cell capable of producing such an antibody.

The invention is further directed to a method for producing the material, and it provides cells producing the antibody or its fragment. The method of producing antibody or its fragment includes the step of (a) immunization an animal with human ICAM-1 protein or protein fragments or a cell expressing human ICAM-1, (b) extracting splenocytes from the immunized animal, (c) fusing the spleen cells of the animal with a myeloma cell line, and (d) screening the hybridoma cells and selecting the desired hybridoma cell that is capable of modulating the differentiation and function of dendritic cells as wells as suppressing the rejection of transplanted organs but not inhibiting the interaction between ICAM-1 and LFA-1. The material can be obtained by in vitro culture or injection into the animals of cells producing the materials. The material can be obtained from the ascites of animals in which the cells producing the materials are intraperitoneally injected. The materials can be purified from the culture supernatant or ascites by ion exchange chromatography or affinity column chromatography.

The invention also includes the hybridoma cell, and the antibody produced by the hybridoma cell, obtained by the method.

The present invention also includes to a pharmaceutical composition for suppressing rejection of transplanted cells or organs. The pharmaceutical composition is comprised of an immunosuppressive agent selected from the group consisting of: an antibody capable of binding ICAM-1 but not inhibiting the interaction of ICAM-1 and LFA-1; and a fragment of an antibody, the fragment being capable of binding ICAM-1 but not inhibiting the interaction of ICAM-1 and LFA. Administration of the antibody or its fragment according to the invention can be carried out using any of the accepted modes of administration of pharmaceutical compositions.

Further, the present invention also relates to the method for suppressing the rejection of transplanted cells or organs, which uses materials selected from the group consisting of antibody or antibody fragments. The antibody or the antibody fragment is preferably selected from the group consisting of monoclonal and polyclonal antibodies, and more preferably it is a human or animal antibody.

The invention also provides methods of detecting ICAM-1 using the antibodies to ICAM-1 disclosed herein. Such detection is useful because ICAM-1 is a marker of inflammation among other disease processes. Antibodies to ICAM-1 can also be sold commercially as research reagents for detecting ICAM-1.

A humanized antibody is an antibody having complementary determining regions (CDRs) from a donor antibody and variable region framework and constant regions from a human antibody. CDRs are typically as defined by Kabat but can alternatively be as defined by Chothia or a composite of Kabat and Chothia definitions (e.g., any residue within a Kabat and/or Chothia CDR). Thus, typically a humanized antibody comprises (i) a light chain comprising three CDRs from a mouse antibody, e.g., MD-2, a variable region framework from a human antibody (which can be, for example, from a mature human antibody, a human germline sequence, a composite of two or more human antibody sequences, or a consensus of human antibody sequences), and a human constant region, and (ii) a heavy chain comprising three CDRs from a mouse antibody, e.g., MD-2, a variable region framework from a human antibody and a human constant region. The heavy and/or light chain variable region frameworks can also include backmutations at a few (usually fewer than 1, 2, 3, 4, 5 or 10) selected positions per chain in which a human residue is replaced with the residue occupying the corresponding position of the mouse antibody (see, Queen et al., U.S. Pat. Nos. 5,530,101 and 5,585,089). Specifically, the amino acids to be replaced in the framework are generally chosen on the basis of their ability to interact with the CDRs. For example, the replaced amino acids can be adjacent to a CDR in the donor antibody sequence or within 4-6 angstroms of a CDR in the humanized antibody as measured in 3-dimensional space.

Substitution of one or more CDR residues or omission of one or more CDRs is also possible provided sufficient CDR residues are retained for retention of binding to ICAM-1. Numerous antibodies have been described in the scientific literature in which one or two CDRs can be dispensed with for binding. Padlan et al., FASEB Journal 9: 133-139 (1995); Vajdos et al (Journal of Molecular Biology, vol. 320, pp. 415-428 (2002); Iwahashi et al., Mol. Immunol. 36:1079-1091, (1999); Tamura et al, Journal of Immunology, 2000, 164:1432-1441 (2000). The substitution of certain regions within CDRs is based on the same principle as omitting dispensable CDRs, namely that only a small subset of CDR residues, the SDR's, actually contact antigen.

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in human acceptor sequence supplying the variable region framework sequences. The number of such substitutions to include reflects a balance of competing considerations Such substitutions are potentially advantageous in decreasing the number of mouse amino acids in a humanized antibody and consequently decreasing potential immunogenicity. However, substitutions can also cause changes of affinity, and significant reductions in affinity are preferably avoided. Positions for substitution within CDRs and amino acids to substitute can also be selected empirically. Empirical substitutions can be conservative or non-conservative substitutions. However, in general empirical substitutions do not have the advantage of mouse to human substitutions in reducing immunogenicity. Empirical substitutions can increase or decrease affinity of the resulting humanized antibody.

In general humanized antibodies with satisfactory binding affinity to ICAM-1 and lack of substantial immunogenicity can be obtained by individual screening of a few variants made according to the above principles above. However, very large numbers of variants can be simultaneously screened using a display selection method such as phage display (see (Dower et al., WO91/17271; McCafferty et al., WO92/001047; and Winter, WO92/20791).

A chimeric antibody is an antibody in which the variable region of a mouse from heavy and light chains (or other rodent) antibody is combined with the heavy and light chain constant region of a human antibody; their construction by means of genetic engineering is well-known. Such antibodies retain the binding specificity of the mouse antibody, while being about two-thirds human. The proportion of nonhuman sequence present in mouse, chimeric and humanized antibodies suggests that the immunogenicity of chimeric antibodies is intermediate between mouse and humanized antibodies.

Usually humanized and chimeric antibodies are of the IgG1, IgG2, IgG3 or IgG4 isotype with a kappa light chain.

The monoclonal antibodies (mAbs) may be of animal (e.g., mouse, rat, hamster or chicken) origin, or they may be genetically engineered. Rodent mAbs are made by standard methods well-known in the art, comprising multiple immunization with ICAM-1 in appropriate adjuvant i.p., i.v., or into the footpad, followed by extraction of spleen or lymph node cells and fusion with a suitable immortalized cell line, and then selection for hybridomas that produce antibody binding to ICAM-1, e.g., see under Examples. Human antibodies can also be made by phage display (see, e.g., Dower et al., WO91/17271; McCafferty et al., WO92/001047; Winter, WO92/20791; and Winter, FEBS Lett. 23:92, 1998) or by using transgenic mice (see, e.g., Lonberg et al., WO93/12227; Kucherlapati WO91/10741) Chimeric and humanized mAbs are preferred embodiments of the invention.

Antibodies are very large, complex molecules (molecular weight of ~150,000 or about 1320 amino acids) with intricate internal structure. A natural antibody molecule contains two identical pairs of polypeptide chains, each pair having one light chain and one heavy chain. Each light chain and heavy chain in turn consists of two regions: a variable ("V") region involved in binding the target antigen, and a constant ("C") region that interacts with other components of the immune system. The light and heavy chain variable regions fold up together in 3-dimensional space to form a variable region that binds the antigen (for example, a receptor on the surface of a cell). Within each light or heavy chain variable region, there are three short segments (averaging 10 amino acids in length) called the complementarity determining regions ("CDRs"). The six CDRs in an antibody variable domain (three from the light chain and three from the heavy chain) fold up together in 3-D space to form the actual antibody binding site which locks onto the target antigen. The position and length of the CDRs have been precisely defined. Kabat, E. et al., Sequences of Proteins of Immunological Interest, U.S. Department of Health and Human Services, 1983, 1987. The part of a variable region not contained in the CDRs is called the framework, which forms the environment for the CDRs.

Antibodies can bind specifically to a particular target protein; that is, bind the target protein preferentially in a mixture of different proteins including the target protein. Specific binding also usually means a dissociation constant (KD) that is less than about $10^{-6}$ M; $10^{-7}$ M, $10^{-8}$ M or $10^{-9}$ M.

Native mAbs of the invention may be produced from their hybridomas. Genetically engineered mAbs, e.g., chimeric or humanized mAbs, may be expressed by a variety of art-known methods. For example, genes encoding their light and heavy chain V regions may be synthesized from overlapping oligonucleotides and inserted together with available C regions into expression vectors (e.g., commercially available from Invitrogen) that provide the necessary regulatory regions, e.g., promoters, enhancers, poly A sites, etc. Use of the CMV promoter-enhancer is preferred. The expression vectors may then be transfected using various well-known methods such as lipofection or electroporation into a variety of mammalian cell lines such as CHO or non-producing myelomas including Sp2/0 and NS0, and cells expressing the antibodies were selected by appropriate antibiotic selection.

Once expressed, the mAbs or other antibodies of the invention may be purified according to standard procedures of the art such as microfiltration, ultrafiltration, protein A or G affinity chromatography, size exclusion chromatography, anion exchange chromatography, cation exchange chromatography and/or other forms of affinity chromatography based on organic dyes or the like. Substantially pure antibodies of at least about 50, 90 or 95% homogeneity are preferred, and 98% or 99% or more homogeneity most preferred, for pharmaceutical uses.

The terms "isolated" and "purified" refer to a material that is substantially or essentially removed from or concentrated in its natural environment and/or undesired contaminants. For example, an isolated antibody is separated from other antibodies directed to other antigens and from other biological materials (e.g., other nucleic acids, proteins, lipids, cellular components) with which it is naturally associated. The antibodies of the invention also include binding fragments of antibodies such as Fv, Fab and F(ab')$_2$; bifunctional hybrid antibodies (e.g., Lanzavecchia et al., Eur. J. Immunol. 17:105, 1987), single-chain antibodies (Huston et al., Proc. Natl. Acad. Sci. USA 85:5879, 1988; Bird et al., Science 242:423, 1988); and antibodies with altered constant regions (e.g., U.S. Pat. No. 5,624,821)

In a preferred embodiment, the present invention provides a pharmaceutical formulation comprising the antibodies described herein. That is, the antibodies can be used in the manufacture of a medicament for treatment of disease. Pharmaceutical formulations (i.e., medicaments) of the antibodies contain the mAb in a physiologically acceptable carrier, optionally with excipients or stabilizers, in the form of lyophilized or aqueous solutions. Acceptable carriers, excipients or stabilizers are nontoxic to recipients at the dosages and concentrations employed, and include buffers such as phosphate, citrate, or acetate at a pH typically of 5.0 to 8.0, most often 6.0 to 7.0; salts such as sodium chloride, potassium chloride, etc. to make isotonic; antioxidants, preservatives, low molecular weight polypeptides, proteins, hydrophilic polymers such as polysorbate 80, amino acids, carbohydrates, chelating agents, sugars, and other standard ingredients known to those skilled in the art.

The mAb is typically present at a concentration of 1-100 mg/ml, e.g., 10 mg/ml.

In another preferred embodiment, the invention provides a method of treating a patient, typically a human, with a disease using an anti-ICAM-1 mAb in a pharmaceutical formulation. The mAb prepared in a pharmaceutical formulation can be administered to a patient by any suitable route, especially parentally by intravenous infusion or bolus injection, intramuscularly or subcutaneously. Intravenous infusion can be given over as little as 15 minutes, but more often for 30 minutes, or over 1, 2 or even 3 hours. The mAb can also be injected directly into the site of disease (e.g., a tumor), or encapsulated into carrying agents such as liposomes. The dose given will be sufficient to alleviate the condition being treated ("therapeutically effective dose") and is likely to be 0.1 to 5 mg/kg body weight, for example 1, 2, 3 or 4 mg/kg, but may be as high as 10 mg/kg or even 15 or 20 mg/kg. A fixed unit dose may also be given, for example, 50, 100, 200, 500 or 1000 mg, or the dose may be based on the patient's surface area, e.g., 100 mg/m$^2$.

The mAb can be administered daily, weekly, biweekly, every other week, monthly or at some other interval, depending, e.g. on the half-life of the mAb, for 1 week, 2 weeks, 4 weeks, 8 weeks, 3-6 months or longer. Repeated courses of treatment are also possible, as is chronic administration. A regime of a dosage and intervals of administration that alleviates or at least partially arrests the symptoms of the disease (biochemical, histologic and/or clinical), including its complications and intermediate pathological phenotypes in development of the disease is referred to as a therapeutically effective regime.

ICAM-1 is a well-known human protein, the amino acid sequence of which is provided by Simmons et al., Nature 331, 624-627 (1988) and GenBank accession 06990.1. LFA is a heterodimer of CD11a and CD18. The amino acid sequence of human CD11a is provided by Larson et al., J. Cell. Biol. 108, 703-712 (1989) and GenBank Y00796.1. The amino acid sequence of human CD18 is provided by Kishimoto et al., Cell 48, 681-690 (1987) and GenBank M15395.1

The present invention is further explained in more detail with reference to the following examples. These examples, however, should not be interpreted as limiting the scope of the present invention in any manner.

Example 1

The Isolation of Hybridoma Cells Capable of Producing Anti-Human ICAM-1 Monoclonal Antibodies To produce ICAM-1/Fc proteins, mRNAs were extracted from PHA-activated human peripheral blood mononuclear cells and the cDNA fragments corresponding to the leader gene segments and extracellular domains of human ICAM-1 were amplified by polymerase chain reaction (PCR). A fragment encoding the extracellular domain of ICAM-1 was cloned with the introduction of NheI and EcoRI sites at the 5' and 3' ends, respectively. To form the fusion construct of human ICAM-1 and human IgG Fc, this fragment was ligated into EcoRI and XhoI-digested plasmid that encoded for the hinge CH2 and CH3 domains of hIgG1. The HEK293T cells were transiently transfected with the plasmids, and ICAM-1/Fc proteins were purified form culture supernatants using protein G column.

Balb/c mice were intraperitoneally immunized with 100 μg of ICAM-1/Fc proteins emulsified in complete Freund's adjuvant and then subsequent twice immunizations were with 100 μg of ICAM-1/Fc proteins emulsified in incomplete Freund's adjuvant at two weeks interval. Two weeks later, immunized mice were boosted with 100 μg of ICAM-1/Fc proteins. The spleen of Balb/c mice was removed 3 days after the last administration to prepare the spleen cell suspension. Monoclonal antibodies were produced by fusing the spleen cells of Balb/c immunized with human ICAM-1/Fc with SP2/0-Ag14 mouse myeloma cells resistant to 9-azaguanine. Cell fusion method followed Koeler and Milstein method (Koeler & Milstein Nature, 1975, 256, 495-497). $10^8$ spleen cells were fused with $10^7$ myeloma cells using 50% polyethylene glycol 4000. The cells were washed and resuspended in Dulbeco's modified Eagle's medium (DMEM) containing 20% fetal bovine serum (FBS), 100 μM hypoxanthine, 0.44 μM aminopterin and 16 μM thymidine (HAT media). The cells were introduced to four 96-well plates and cultured at 37° C. in a 5% $CO_2$ incubator.

When colonies were formed after two weeks, the supernatant were screened using human ICAM-1-transfected HEK 293T cells. Both ICAM-1-transfected and wild type HEK293T cells were stained with culture supernatant and cells producing supernatant reactive against ICAM-1-transfected 293T cells but not wild type 293T cells were selected. Cells taken from the positive wells were subcloned 0.5 cell per well by limiting dilution assay to produce stable hybridoma clone with high reactivity of antibody.

This experiment resulted in the identification and cloning of three separate hybridoma lines which produce anti-ICAM-1 monoclonal antibodies. One of these hybridoma lines produced IgG1 antibody with a kappa light chain and was given the designation MD-2. The hybridoma named for MD-2 was deposited at Cancer Research Institute located on Seoul National University, College of Medicine, 28 Yongon-dong, Chongno-Gu, Seould, 110-744, Republic of Korea on Dec. 24, 2008, and received as an accession number of KCLRF-BP-00198. This deposit will be maintained at an authorized depository and replaced in the event of mutation, nonviability or destruction for a period of at least five years after the most recent request for release of a sample was received by the depository, for a period of at least thirty years after the date of the deposit, or during the enforceable life of the related patent, whichever period is longest. All restrictions on the availability to the public of this cell line will be irrevocably removed upon the issuance of a patent from the application.

As shown in FIG. 1, ICAM-1-transfected 293T cells were positively stained by MD-2 antibody as well as a known anti-human ICAM-1 antibody, R6-5-D6, while either antibody was not reactive against wild type untransfectant.

Once an exemplary antibody has been identified (e.g., MD-2) other antibodies binding to the same or overlapping epitope on ICAM-1 can be identified by a competitive binding assay. Two antibodies bind to the same or overlapping epitope if each competitively inhibits (blocks) binding of the other to the antigen. That is, a 1×, 5×, 10×, 20× or 100× excess of one antibody inhibits binding of the other by at least 50% but preferably 75%, 90% or even 99% as measured in a competitive binding assay (see, e.g., Junghans et al., Cancer Res. 50:1495, 1990). The competitive binding assay can be performed on intact ICAM-1, the extracellular region thereof including five immunoglobulin-like domains, or on domain 1 separated from the other immunoglobulin-like domains. Alternatively, the method of Jespers et al., Biotechnology 12:899, 1994, which is incorporated herein by reference, may be used to guide the selection of mAbs having the same epitope and therefore similar properties to the archtypal mAb, MD-2. Using phage display, first the heavy chain of the archtypal antibody is paired with a repertoire of (preferably human) light chains to select an HGF-binding mAb, and then the new light chain is paired with a repertoire of (preferably human) heavy chains to select a (preferably human) ICAM-1-binding mAb having the same epitope as the archtypal mAb.

Variants of MD-2 and its humanized and chimeric forms can also be made by substitution of amino acids, particularly at variable region framework positions. Such substitutions can be conservative or nonconservative. For purposes of classifying amino acids substitutions as conservative or nonconservative, amino acids may be grouped as follows: Group I (hydrophobic sidechains): Met, Ala, Val, Leu, Ile; Group II (neutral hydrophilic side chains): Cys, Ser, Thr; Group III (acidic side chains): Asp, Glu; Group IV (basic side chains): Asn, Gln, His, Lys, Arg; Group V (residues influencing chain orientation): Gly, Pro; and Group VI (aromatic side chains): Trp, Tyr, Phe. Conservative substitutions are those that involve substitutions between amino acids in the same group. Variants can be screened for binding to ICAM-1, particularly the first domain thereof, optionally in competition with the MD-2 antibody. The heavy and light chains of a variant preferably show at least 90, or 95% amino acid sequence identity with a reference antibody, such as MD-2, particularly in the CDR regions. Sequence identity is determined by comparing heavy or light chain variable regions maximally aligned with heavy or light chain variable regions of a reference antibody by Kabat numbering not counting gaps.

Example 2

Mapping of Antibody Binding Domain

ICAM-1 has a structure composed of five immunoglobulin-like (Ig-like) domains, a transmembrane domain and a cytoplasmic domain (Cell. 1992, 68:71-81). In order to localize the site of MD-2 binding to a particular ICAM-1 Ig-like domain, two kinds of chimeric cDNAs were made that code for human domain 1/murine domains 2-5 including murine transmembrane and cytoplasmic domains (h1m2345) and for human domains 1-2/murine domains 3-5 (h12m345), using human and murine ICAM-1 cDNA clones. The overlapping PCR technique was used to construct these chimeric mutants. The cDNA containing human domain 1 (h1) was first amplified using the primers as follows: 5' primer GAA TTC ATG GCT CCC AGC AGC CCC CGG CCC GCG CT (SEQ ID NO: 1); 3' primer AGG TCT CAG CTC CAC CCG TTC TGG AGT CCA GTA CAC GGT GAG GAA G (SEQ ID NO: 2). Primers for the generation of murine domains 2-5, a transmembrane domain and a cytoplasmic domain (m2345) were as follows: 5' primer, CTG GAC TCC AGA ACG G GTG GAG CTG AGA CCT CTG CCA GCC TGG CAG (SEQ ID NO: 3); 3' primer GGA TCC GGG AGG TGG GGC TTG TCC CTT GAG TTT TAT GGC (SEQ ID NO: 4). These two kinds of cDNA were mixed and re-amplified using SEQ ID NO: 1 and SEQ ID NO: 4 primers and the final product (h1m2345) was cloned in pcDNA3.1 vector. The mutant that code h12m345 was also cloned in the way similar to that for h1m2345 using the following primers: 5' primer for h12, GAA TTC ATG GCT CCC AGC AGC CCC CGG CCC GCG CT (SEQ ID NO:5); 3' primer for h12, GGT AGC TGG AAG ATC AAA GGT CTG GAG CTG GTA GGG GGC CGA GGT (SEQ ID NO:6); 5' primer for m345, CAG CTC CAG ACC TTT GAT CTT CCA GCT ACC ATC CCA AAG CTC GAC ACC (SEQ ID NO:7); 3' primer for m345, GGA TCC GGG AGG TGG GGC TTG TCC CTT GAG TTT TAT GGC (SEQ ID NO:8).

Figure 2:
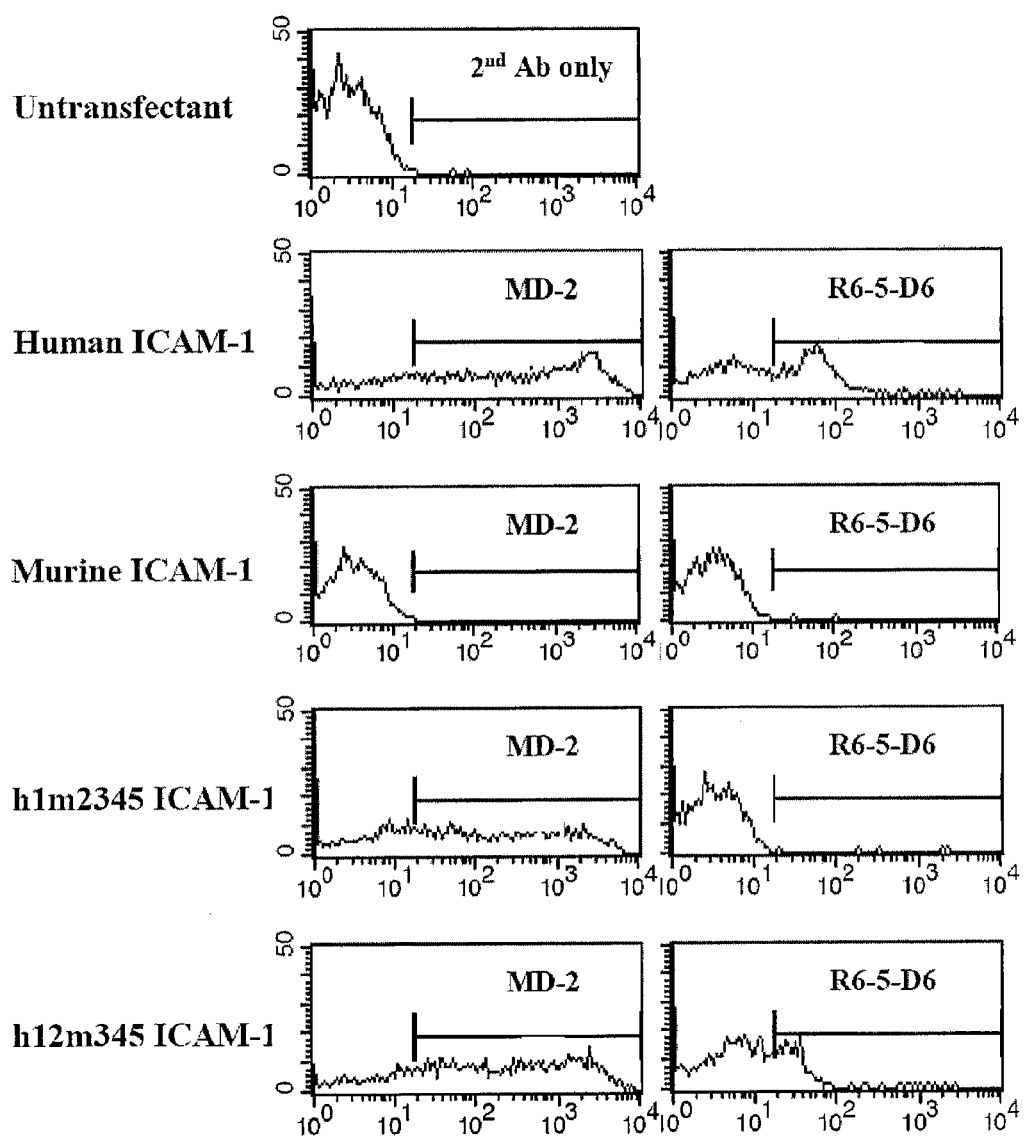
FIG. 2 shows a photograph of the reactivity of MD-2 and R6-5-D6 antibodies on the HEK293T cells transfected with h1m2345 and h12m345 ICAM-1 mutants

The entire construct were sequenced to confirm that the corrected junctions had been obtained and then plasmid DNA were transfected to HEK293T cells using calcium phosphate precipitation method. After incubation of HEK293T cells with coprecipitates of calcium phosphate and plasmid DNA for 16-20 hrs, media were replaced with 10 ml of fresh solution and the cells were incubated for another 24 hours. Then, transfectant was stained with MD-2 or R6-5-D6 antibody in ice. After incubation for 30 min, cells were washed three times in phosphate buffered saline (PBS) with 5% fetal calf serum and 0.1% azide and incubated for 30 min with FITC-conjugated goat anti-mouse Ig antibody ($2^{nd}$ Ab). After a further three washes, flow cytometric analysis was performed to test for their ability to react with each antibody (FIG. 2). As the negative control, cells stained with only $2^{nd}$ Ab were used. As shown in FIG. 2, full human ICAM-1 transfectant was positively stained with both MD-2 and R6-5-D6 antibodies, whereas either antibodies were not reactive with full mouse ICAM-1 transfectant, indicating these anti-human ICAM-1 antibodies are not cross-reactive with mouse ICAM-1. In the case of chimeric mutant, MD-2 antibody reacted with both chimera, h1m2345 and h12m345, while R6-5-D6 antibody that had been previously assigned to the domain 2 (Cell. 1992, 68:71-81) were reactive only with the h12m345 chimera. Thus, all these results indicated that MD-2 antibody is specific for epitope on domain 1 and R6-5-D6 antibody map to domain 2.

Example 3

Effect of Anti-ICAM-1 Antibody in Mixed Lymphocyte Reaction

Although the LFA-1-binding site is located in domain of ICAM-1, domain 2 had been known to play an essential role in the confirmation of domain 1 (Cell. 1992, 68:71-81). Thus, some of antibodies blocking the interaction between LFA-1 and ICAM-1 mapped to the domain 1, whereas other antibodies that map the domain 2 such as R6-5-D6 antibody are also able to inhibit this interaction (Cell. 1992, 68:71-81). We also investigated whether LFA-1 and ICAM-1 interaction could be affected by MD-2 antibody.

Figure 3:
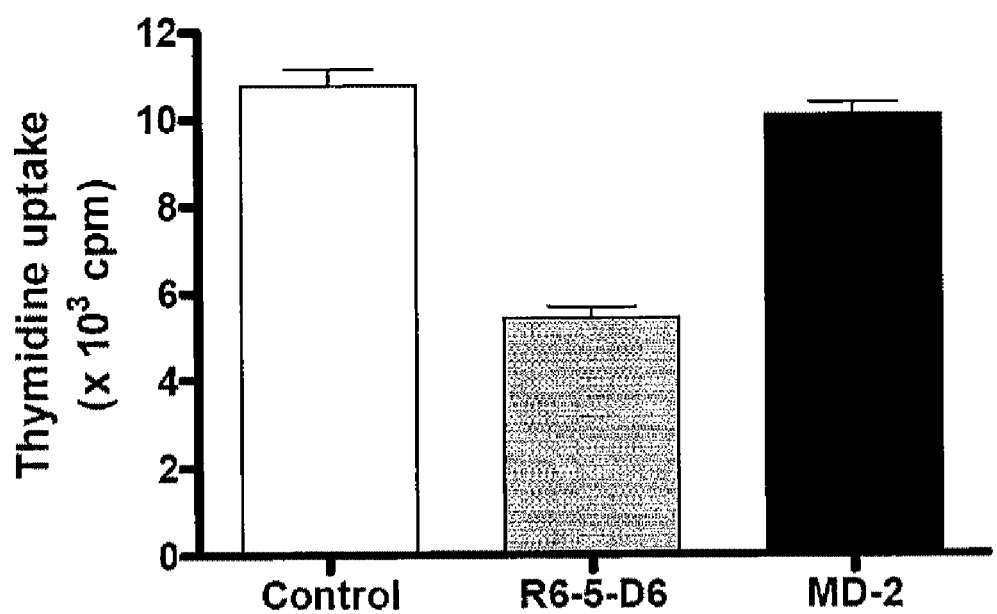
FIG. 3 shows the result of thymidine uptake after mixed lymphocyte reaction in the presence of MD-2 or R6-5-D6 antibody.

When lymphocytes from two unrelated persons are cultured in each other's presence, proliferation of lymphocytes are observed and this mixed lymphocyte reaction (MLR) has been known to dependent on the ICAM-1/LFA-1 interaction (Proc. Natl. Acad. Sci. USA. 1988, 85:3095-3099). Thus, MLR assay was performed to assess whether anti-ICAM-1 antibody, MD-2 is able to interfere with LFA-1 adhesion to ICAM-1. Fresh blood cells were obtained from two unrelated donors and peripheral blood mononuclear cells were collected after overly on Ficoll-hypaque (Pharmacia, Uppsala, Sweden) and centrifugation at 2,000 rpm for 20 minutes and re-suspended in DMEM with 10% fetal bovine serum. $CD4^{+}$ T cells were purified from one donor using magnetic activated cell sorting (MACS) system described in EXAMPLE 5. Cell from the other donor were irradiated with 2000 cGy using cobalt radiation source. Then after mixing cells from each donor, mixed cells were plated in flat-bottomed, 96 well tissue culture plates at 1×10⁶ cells/well and cultured in presence or absence of anti-ICAM-1 antibodies (20 μg/ml). The cultures were pulsed with [³H]thymidine (0.5 μCi/well) after 3 days, harvested onto glass fiber filters 16 hours later, and then counted on a liquid scintillation β counters. As shown in FIG. 3, anti-ICAM-1 blocking antibody, R6-5-D6 suppressed MLR, while the proliferation of cultured cells was not affected by MD-2 antibody. These results suggest that MD-2 antibody have no activity to block the interaction of ICAM-1 and LFA-1.

Example 4

Comparison of Binding Epitope of MD-2 and R6-5-D6 Antibodies

Figure 4:
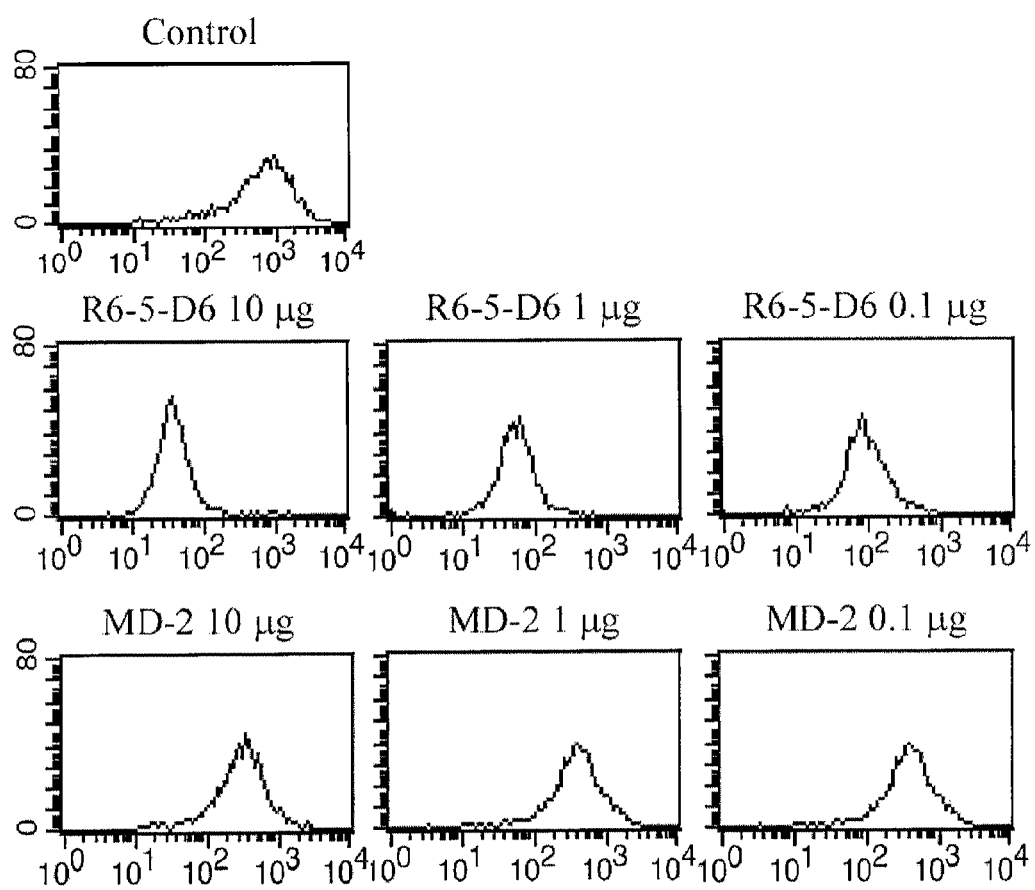
FIG. 4 shows a photograph of the reactivity of R6-5-D6 antibody on the human ICAM-1-positive DU145 cells after pre-incubation with MD-2 or R6-5-D6 antibody.

The results from Example 2 suggest that binding epitope of MD-2 antibody may be different form that of R6-5-D6. To confirm this suggestion, cross-blocking study in which the biding of one antibody in turn is competed for by the other antibody (Cell. 1992, 68:71-81) was performed. 10, 1, or 0.1 μg of MD-2 or R6-5-D6 antibody was preincubated with ICAM-1-positive DU145 cells for 30 min on ice and washed twice prior to incubation with 1 μg of FITC-conjugated R6-5-D6 antibody. Control used was omission of competing antibodies from the assay. Cells were washed twice and analyzed using flow cytometry. As shown in FIG. 4, Binding of FITC-conjugated R6-5-D6 antibody was inhibited by preincubation with unconjugated R6-5-D6 antibody in a dose-dependent manner. Whereas the preincubation of DU145 cells with MD-2 antibody had no effect on the binding of R6-5-D6 antibody, indicating that the binding epitope of MD-2 antibody is different from that of R6-5-D6 antibody.

Example 5

Figure 5A:
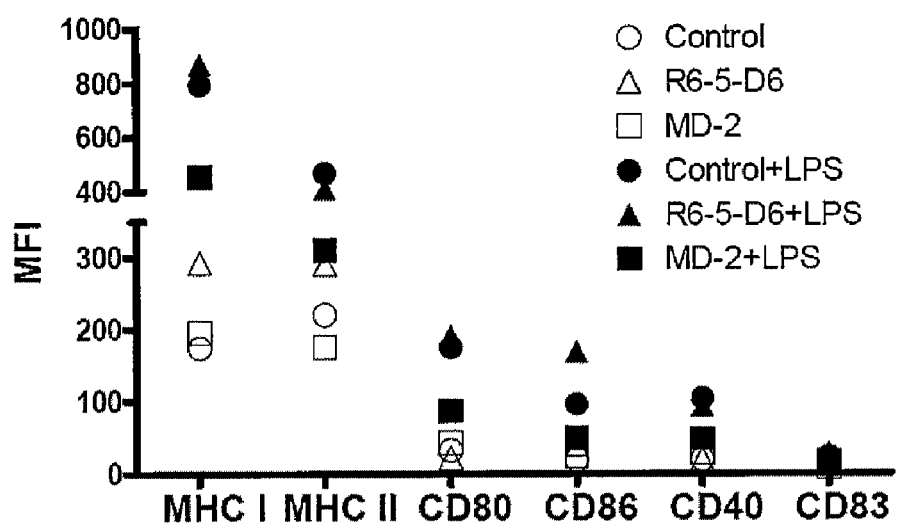
FIGS. 5A and 5B shows the expression level of various molecules on the surface of dendritic cells (A) and cytokine concentration in the culture media of dendritic cells (B) after treatment of indicated antibodies.
Figure 5B:
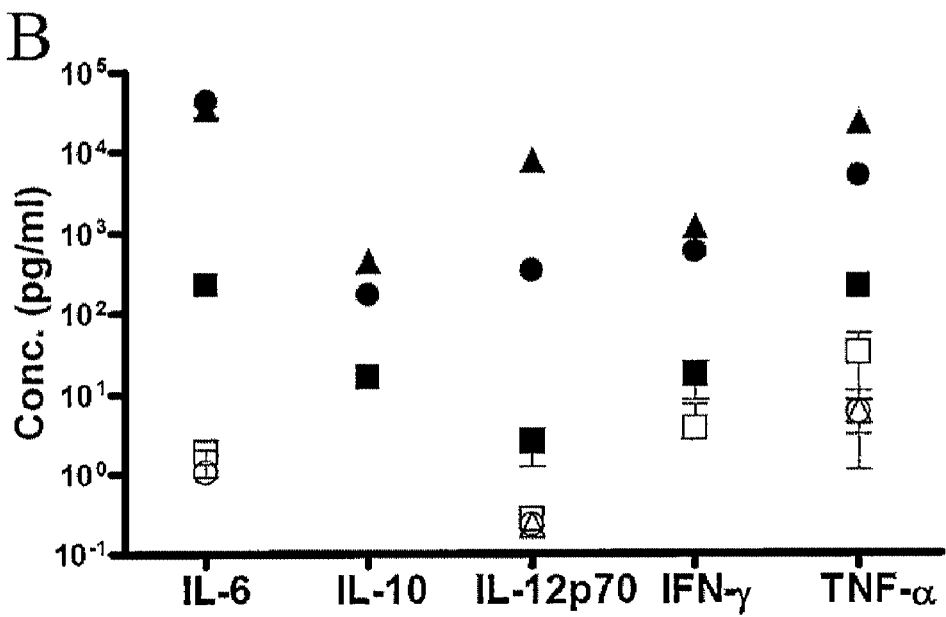

Effect of Anti-ICAM-1 Antibody in the Differentiation of Monocyte-Derived Dendritic Cells Peripheral blood mononuclear cells were isolated from healthy donor blood by Ficoll-hypaque density-gradient centrifugation. After washing twice with PBS, cells were re-suspended in MACS buffer at the concentration of 1×10⁸ cells/ml and then incubated with anti-CD14 magnetic bead (20 μl/10⁷ cells; Miltenyi Biotec, Bergisch Gladbach, Germany) in ice for 15 minutes, followed by magnetic separation using MACS (Milteny-Biotech). Purified CD14⁺ monocytes were re-suspended in RPMI with 10% FBS and were cultured for 6 days with granulocytes-macrophage colony stimulating factor (GM-CSF, 1000 U/ml) and IL-4 (1000 U/ml). The culture was supplemented with antibody (10 mg/ml) on day 0 and day 3 and LPS was added to the culture medium on day 6. One day later, cultured cells were harvested and expression of MHC class I, MHC class II, CD80, CD86, CD40, and CD83 was examined by flow cytometry. ELISA was also done to measure the amount of IL-6, IL-10, IL-12p70, IFN-γ and TNF-α in culture media. When CD14⁺ monocytes were cultured in the presence of GM-CSF and IL-4, they are able to differentiate into the immature DCs and LPS treatment induces the maturation of immature DCs. The mean fluorescence intensity (MFI) of indicated antigens and the cytokine concentration in each culture media was displayed in FIG. 5B. As expected, LPS treatment in immature DC enhanced the expression of MHC class I, MHC class II, CD80, CD86, and CD40 and cytokine production. Up-regulation of the surface expression of these molecules and cytokine production in DCs by LPS stimulation was not suppressed by pre-treatment of anti-ICAM-1 blocking antibody, R6-5-D6. Unlike R6-5-D6 antibody, however, pretreatment of MD-2 antibody prior to LPS stimulation significantly suppressed the up-regulation of surface molecule expression and cytokine production in the DCs, indicating that MD-2 antibody is able to inhibit the maturation of monocyte-derived DCs.

Example 6

Generation of Humanized Mice

To investigate the in vivo effect of anti-ICAM-1 antibodies, humanized mice were generated by engraftment of human hematopoietic stem cells in immunodeficient mice according the procedure by Ito, M. et al., Blood. 2002, 100:3175-82.

Figure 6A:
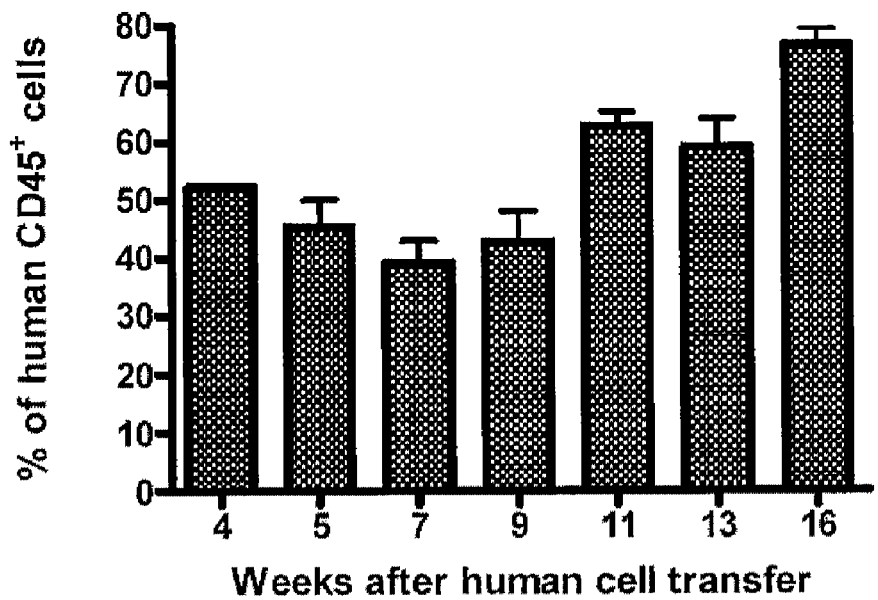
FIGS. 6A and B shows the kinetics of the generation of $CD45^+$ human leukocytes (A) and $CD3^+$ human T cells (B) in peripheral blood of humanized mice.
Figure 6B:
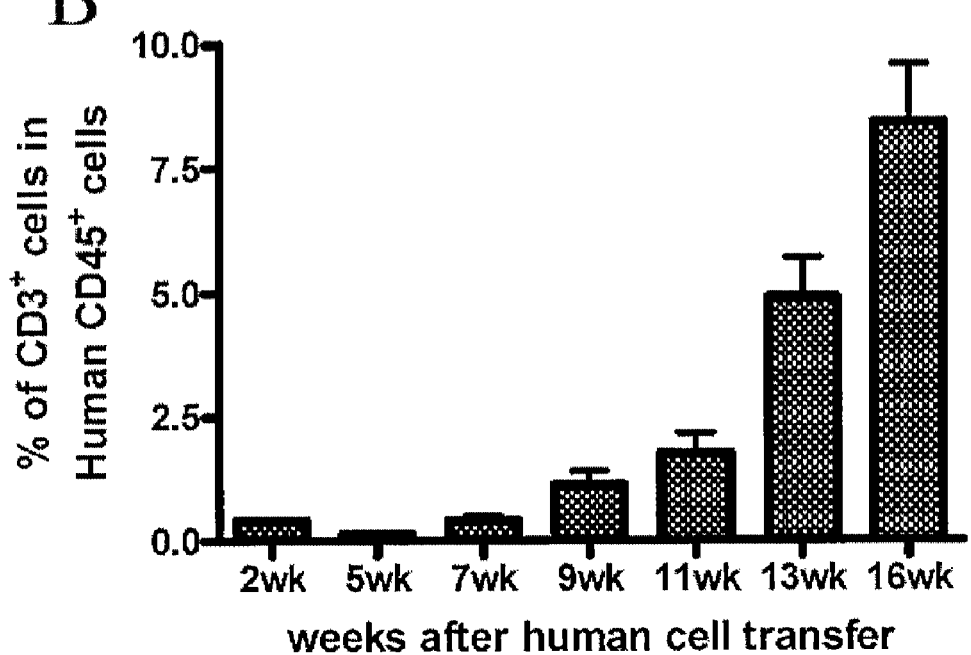

Umbilical cord blood cells were collected during normal full-term delivers and mononuclear cells were separated by Ficoll-hypaque centrifugation. Separated mononuclear cell were suspended at 3.3×10⁸ cells/ml in PBS containing 5% FBS and 2 mM EDTA and incubated in ice for 30 minutes with Fc blocking antibody, followed by incubation in ice for 30 minutes with anti-CD34 magnetic beads (Milteny-Biotech). After twice washing, bead-attached cells were collected by magnetic separation using MACS. After two rounds of magnetic separation, purity was evaluated by flow cytometry and no less than 95% of the collected cells were CD34⁺. 8- to 12-wekk-old NOD.SCID/γc$^{null}$ mice (Central Institute for Experimental Animals, Japan) were irradiated with 240 cGy using cobalt radiation source and 1 day later 1×10⁵ CD34⁺ cells were injected into the each mouse through the tail vein. Peripheral blood was taken from the retro-orbital venous plexus sequentially between weeks 4 and 16 after transplantation and stained with anti-human CD45 and anti-human CD3 antibodies for flow cytometry. FIG. 6 shows the chimeric rates of human cells in the peripheral blood of mice at the indicated weeks after cell transplantation. Human leukocytes were detected in all mice and more than 60% of leukocytes in peripheral blood were human CD45⁺ at 11 weeks after transplantation (FIG. 6A) and approximately 10% of the human CD45⁺ cells expressed CD3 at 16 weeks after transplantation (FIG. 6B).

Example 7

Figure 7:
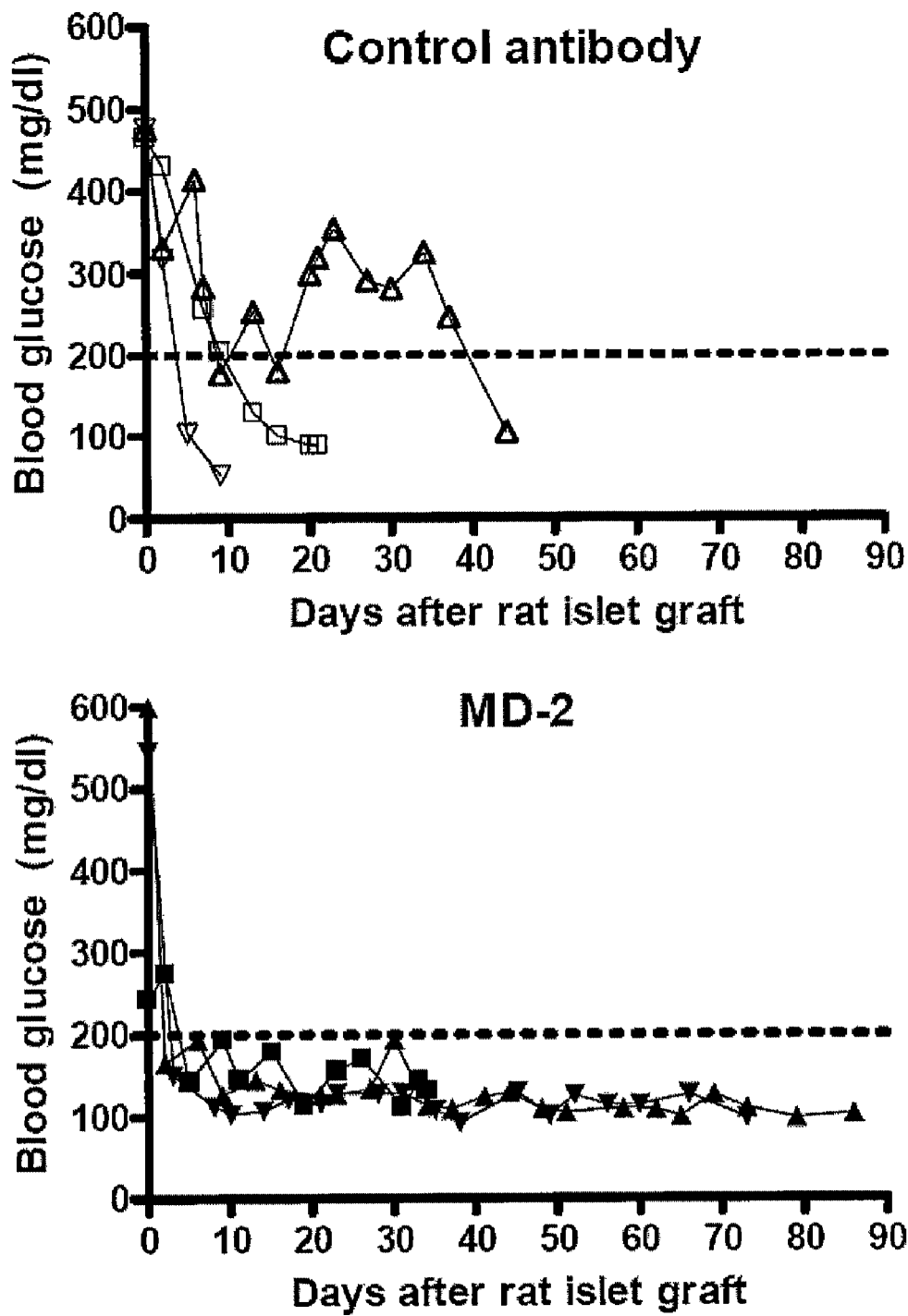
FIG. 7 shows the peripheral blood glucose level in humanized mice in which diabetes was induced by streptozotocin and then rat islets were transplanted.

Effect of Anti-ICAM-1 Antibody in Suppressing the Rejection of Transplanted Xenogenic Islet In order to demonstrate the effect of MD-2 antibody in suppressing the transplantation rejection, islet xenograft model was used. Humanized mice were rendered diabetic by twice intraperitoneal injection of 100 mg/kg streptozotocin (Sigma, St. Louis, Mo.) dissolved in citrate buffer, pH 4.5 on 2 consecutive days. Blood glucose levels were determined using ACCU-CHECK glucometer (Roche, Mannheim, Germany) at 3 day after streptozotocin injection and only animals with blood glucose >250 mg/dl were used as diabetic recipients. Islets for transplantation were isolated from the Sprague-Dolley rats by stationary collagenase digestion (0.07% type XI collagenase, Sigma), followed by discontinuous Ficoll (Ficoll 400, Pharmacia) density gradient as previous described (Transplantation. 2000, 69:1567-1571). After isolation, crude islet cells were over-night cultured in DMEM with 10% FBS at 37° C. in a 5% CO₂ incubator and then 500 islets were transplanted into the left renal subcapsular space of each diabetic humanized mouse at 4 day after streptozotocin injection. Anti-ICAM-1 antibody (300 μg/mouse) was injected intraperitoneally at 6 and 3 day before islet transplantation. Control group of animal received irrelevant mouse IgG. Return of blood glucose levels to less than 200 mg/dl was used as an indicator of graft function, and a sudden rise to levels >250 mg/dl on 2 consecutive days was indicative of rejection. As shown in FIG. 7, mice of control group died or graft were rejected within 3 weeks after islet transplantation, while blood glucose level was maintained still in less than 200 mg/dl throughout the follow-up period in all mice received MD-2 antibody prior to islet graft.

Figure 8:
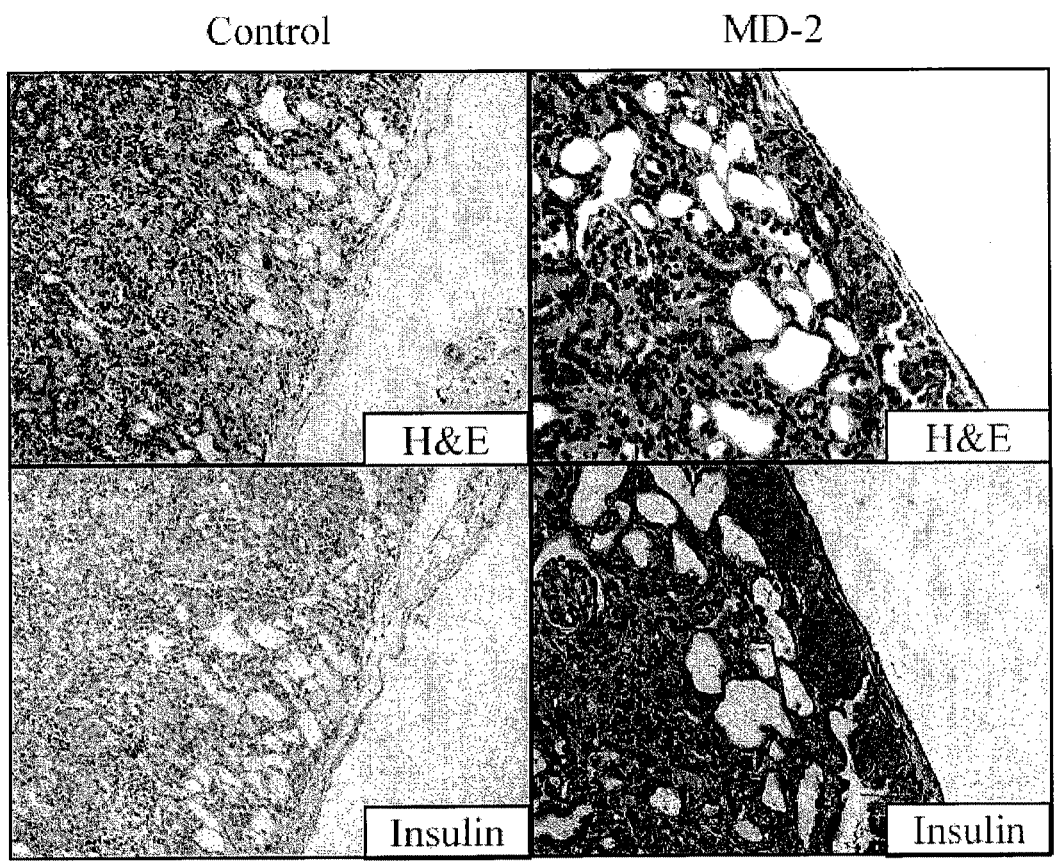
FIG. 8 shows the photograph of hematoxylin and eosin (H&E) staining and immunohistochemical staining for insulin in islet-grafted kidneys extracted from each mouse treated with indicated antibodies.

Mice were sacrificed when they showed a morbid condition and left nephrectomy specimen was analyzed histologically for evidence of graft rejection. Control mice were sacrificed at day 9, 21 and 44 post-grafting, In MD-2 antibody-treated group, mice were sacrificed at day 34, 77 and 87 post-grafting. Nephrectomy specimen from each mice was fixed in 10% neural formalin, embedded in paraffin and then serially sectioned in 4 μm thickness for routine hematoxylin-eosin staining or immunohistochemistry. Staining for insulin utilized a primary goat antiserum to human insulin (DAKO, Carpenteria, Calif.) followed by the anvidin-biotin peroxidase method and diaminobenzidine as substrate. As can be seen in FIG. 8, infiltration of mononuclear cells was evident in the subcapsular area of mice received control antibody and immunohistochemical staining failed to reveal the viable islet in these mice. However unlike to control mice, graft survival was still evident and mononuclear cells infiltrate was not observed in MD-2-treated mice. Moreover, the grafted islets continued to produce insulin. Thus, MD-2 treatment prior to transplantation is able to lead the prolonged survival of the islet xenografts.

All publications, patents and patent applications cited are herein incorporated by reference in their entirety for all purposes to the same extent as if each individual publication, patent and patent application was specifically and individually indicated to be incorporated by reference in its entirety for all purposes.

What is claimed is:

1. A monoclonal antibody that binds to human intracellular adhesion molecule 1 (ICAM-1), wherein the antibody is designated MD-2 and is produced by a hybridoma deposited as accession number KCLRF-BP-00198.

2. A pharmaceutical composition comprising the antibody of claim 1.

3. The pharmaceutical composition according to claim 2, wherein the antibody is in isolated form.

4. A pharmaceutical composition for modulating the differentiation of dendritic cells via binding ICAM-1, comprising the antibody according to claim 1.

5. A pharmaceutical composition for suppressing refection of transplanted cells or organs, or suppressing graft versus host disease by transplanted hematopoietic cells, comprising the antibody according to claim 1.

6. A monoclonal antibody that binds to human ICAM-1 comprising a heavy chain and a light chain, the heavy chain comprising three CDRs from the heavy chain of an antibody produced by a hybridoma deposited as accession number KCLRF-BP-00198 and the light chain comprising three CDRs from the light chain of an antibody produced by a hybridoma deposited as accession number KCLRF-BP-00198.

7. The antibody according to claim 6, wherein the antibody is a chimeric or humanized antibody.

8. A pharmaceutical composition comprising the antibody according to claim 6 for suppressing resection of transplanted cells or organs, or suppressing graft versus host disease by transplanted hematopoietic cells.

9. A pharmaceutical composition comprising a monoclonal antibody that binds to human ICAM-1 comprising a heavy chain and a light chain, the heavy chain comprising three CDRs from the heavy chain of an antibody produced by a hybridoma deposited as accession number KCLRF-BP-00198 and the light chain comprising three CDRs from the light chain of an antibody produced by a hybridoma deposited as accession number KCLRF-BP-00198.

10. The pharmaceutical composition according to claim 9, wherein the antibody is chimeric antibody or humanized antibody.

11. A hybridoma producing an antibody, wherein the antibody binds to domain 1 of human intercellular adhesion molecules-1 (ICAM-1), which is deposited as accession number KCLRF-BP-00198.

* * * * *

SEQUENCE LISTING

```
<160> NUMBER OF SEQ ID NOS: 8

<210> SEQ ID NO 1
<211> LENGTH: 35
<212> TYPE: DNA
<213> ORGANISM: Artificial Sequence
<220> FEATURE:
<223> OTHER INFORMATION: synthetic forward primer for the cDNA
      containing human domain 1 (h1)

<400> SEQUENCE: 1
gaattcatgg ctcccagcag cccccggccc gcgct                               35

<210> SEQ ID NO 2
<211> LENGTH: 46
<212> TYPE: DNA
<213> ORGANISM: Artificial Sequence
<220> FEATURE:
<223> OTHER INFORMATION: synthetic reverse primer for the cDNA
      containing human domain 1 (h1)

<400> SEQUENCE: 2
aggtctcagc tccacccgtt ctggagtcca gtacacggtg aggaag                   46

<210> SEQ ID NO 3
<211> LENGTH: 46
<212> TYPE: DNA
<213> ORGANISM: Artificial Sequence
<220> FEATURE:
<223> OTHER INFORMATION: synthetic forward primer for generation of
      murine domains 2-5, a transmembrane domain and a cytoplasmic
      domain (m2345)

<400> SEQUENCE: 3
ctggactcca gaacgggtgg agctgagacc tctgccagcc tggcag                   46

<210> SEQ ID NO 4
<211> LENGTH: 39
<212> TYPE: DNA
<213> ORGANISM: Artificial Sequence
<220> FEATURE:
<223> OTHER INFORMATION: synthetic reverse primer for generation of
      murine domains 2-5, a transmembrane domain and a cytoplasmic
      domain (m2345)

<400> SEQUENCE: 4
ggatccggga ggtggggctt gtcccttgag ttttatggc                           39
```

```
<210> SEQ ID NO 5
<211> LENGTH: 35
<212> TYPE: DNA
<213> ORGANISM: Artificial Sequence
<220> FEATURE:
<223> OTHER INFORMATION: synthetic forward primer h12

<400> SEQUENCE: 5
gaattcatgg ctcccagcag cccccggccc gcgct                          35

<210> SEQ ID NO 6
<211> LENGTH: 45
<212> TYPE: DNA
<213> ORGANISM: Artificial Sequence
<220> FEATURE:
<223> OTHER INFORMATION: synthetic reverse primer h12

<400> SEQUENCE: 6
ggtagctgga agatcaaagg tctggagctg gtaggggcc gaggt                45

<210> SEQ ID NO 7
<211> LENGTH: 48
<212> TYPE: DNA
<213> ORGANISM: Artificial Sequence
<220> FEATURE:
<223> OTHER INFORMATION: synthetic forward primer m345

<400> SEQUENCE: 7
cagctccaga cctttgatct tccagctacc atcccaaagc tcgacacc            48

<210> SEQ ID NO 8
<211> LENGTH: 39
<212> TYPE: DNA
<213> ORGANISM: Artificial Sequence
<220> FEATURE:
<223> OTHER INFORMATION: synthetic reverse primer m345

<400> SEQUENCE: 8
ggatccggga ggtgggctt gtccttgag ttttatggc                        39
```